(12) United States Patent
Joo

(10) Patent No.: US 11,666,621 B2
(45) Date of Patent: Jun. 6, 2023

(54) COMPOSITION HAVING INHIBITORY EFFECT ON VIRUS AND BACTERIA

(71) Applicant: Chul-Gue Joo, Yongin-si (KR)

(72) Inventor: Chul-Gue Joo, Yongin-si (KR)

( * ) Notice: Subject to any disclaimer, the term of this patent is extended or adjusted under 35 U.S.C. 154(b) by 6 days.

(21) Appl. No.: 16/641,425

(22) PCT Filed: Aug. 24, 2018

(86) PCT No.: PCT/KR2018/009834
§ 371 (c)(1),
(2) Date: Jun. 17, 2020

(87) PCT Pub. No.: WO2019/039919
PCT Pub. Date: Feb. 28, 2019

(65) Prior Publication Data
US 2020/0397843 A1 Dec. 24, 2020

(30) Foreign Application Priority Data
Aug. 24, 2017 (KR) .................. 10-2017-0106965

(51) Int. Cl.
*A61K 36/87* (2006.01)
*A61P 31/02* (2006.01)
*A61K 36/53* (2006.01)
*A61K 36/752* (2006.01)

(52) U.S. Cl.
CPC .............. *A61K 36/87* (2013.01); *A61K 36/53* (2013.01); *A61K 36/752* (2013.01); *A61P 31/02* (2018.01)

(58) Field of Classification Search
None
See application file for complete search history.

(56) References Cited

U.S. PATENT DOCUMENTS

| | | | | |
|---|---|---|---|---|
| 7,867,523 B2* | 1/2011 | Vanterpool | .......... | A61K 31/715 424/641 |
| 2003/0224072 A1* | 12/2003 | Frome | .................... | A61K 36/61 424/736 |
| 2014/0255525 A1* | 9/2014 | Smith | .................... | A61K 36/73 424/727 |

FOREIGN PATENT DOCUMENTS

| KR | 10-2012-0036924 A | 4/2012 |
|---|---|---|
| KR | 10-2016-0009330 A | 1/2016 |
| KR | 10-2016-0016976 A | 2/2016 |

OTHER PUBLICATIONS

Devbrat Yadav, et al., "Antimicrobial Properties of Black Grape (*Vitis vinifera* L.) peel extracts against antibiotic-resistant pathogenic bacteria and toxin producing molds", Indian Journal of Pharmacology, Nov.-Dec. 2015, pp. 663-667, vol. 47, No. 6.
A. Fabio, et al., "Screening of the Antibacterial Effects of a Variety of Essential Oils on Microorganisms Responsible for Respiratory Infections", Phytotherapy Research, 2007, pp. 374-377, vol. 21.
Wahab O. Okunowo, et al., "Essential Oil of Grape Fruit (*Citrus paradise*) Peels and Its Antimicrobial Activities", American Journal of Plant Sciences, 2013, vol. 4, No. 1-9.
International Search Report for PCT/KR2018/009834 dated Mar. 5, 2019 [PCT/ISA/210].
Written Opinion for PCT/KR2018/009834 dated Mar. 5, 2019 [PCT/ISA/237].
Korean Office Action for 10-2017-0106965 dated May 15, 2018.

* cited by examiner

*Primary Examiner* — Susan Hoffman
(74) *Attorney, Agent, or Firm* — Sughrue Mion, PLLC

(57) ABSTRACT

The present invention relates to an antimicrobial composition comprising a grape extract, a lemon extract, and a lavender extract. Not only providing excellent antiviral, antibacterial, and antifungal effects but also being derived from natural products, the composition of the present invention can be used safely without toxicity and side effects and can find various applications in medicinal products, foods, cosmetic products, quasi-drugs, etc.

6 Claims, 2 Drawing Sheets

|  | Control group Untreated with virus | Control group treated with virus | Experimental group treated with Virus+Sample 4 | Experimental group treated with virus+Sample 5 | Experimental group treated with virus+Sample 6 | Experimental group treated with virus+Sample 7 |
|---|---|---|---|---|---|---|
| EV71 | - | + | + | + | + | + |
| Sample 4 | - | - | + | - | - | - |
| Sample 5 | - | - | - | + | - | - |
| Sample 6 | - | - | - | - | + | - |
| Sample 7 | - | - | - | - | - | + |
| VP0 Capsid protein |  | ▬ |  | ▬ | ▬ | ▬ |
| α-Tubulin | ▬ | ▬ | ▬ | ▬ | ▬ | ▬ |

COMPOSITION HAVING INHIBITORY EFFECT ON VIRUS AND BACTERIA

CROSS-REFERENCE TO THE RELATED APPLICATION

This application is a National Stage of International Application No. PCT/KR2018/009834 filed Aug. 24, 2018, claiming priority based on Korean Patent Application No. 10-2017-0106965 filed Aug. 24, 2017, the entire of which are incorporated herein by reference.

TECHNICAL FIELD

The present invention provides an antimicrobial composition comprising a grape extract, a lemon extract and a lavender extract.

BACKGROUND ART

Viruses are a representative pathogen that causes diverse infectious diseases such as smallpox, influenza, AIDS, etc. Due to their very small size, the existence of viruses was not clearly known until the 1900s. Now, the structures, functions, and mechanisms of viruses are well known, and diverse vaccines and therapeutic agents are being developed. However, the different reproduction routes and genetic mutations, etc. make it difficult to develop effective therapeutic agents. For example, a hand-foot-mouth disease caused by infection with viruses in the Picornaviridae family (e.g., enterovirus 71) is highly contagious and may be accompanied by fever, vomiting, diarrhea, headache and meningitis mainly in infants. Although the hand-foot-mouth becomes a big social issue, effective vaccines and therapeutic agents have not yet been developed.

Meanwhile, infection with diverse microorganisms such as bacteria, fungi, yeasts, etc., as well as viruses, is the main cause of diseases for mammals including humans. Numerous antiviral agents and antibacterial agents have been developed and are in use, but some synthetic drugs are reported to have side effects. In addition, continuous evolution of microorganisms contributes to drug tolerance, leading to reduction of drug's effect. Therefore, there is a demand for the development of antimicrobial agents derived from natural sources which are safe with no side effects, while having excellent antimicrobial activity.

Accordingly, the present inventor has found that a mixture composition of natural extracts obtained from grape, lemon and lavender has an excellent effect of inhibiting the activity of diverse microorganisms to an unexpected degree, and completed the present invention.

Technical Problem

One purpose of the present invention is to provide an antimicrobial composition derived from natural products, and more specifically to provide a pharmaceutical composition, a food composition, a cosmetic composition and a detergent composition having antimicrobial activity.

Technical Solution

One aspect of the present invention is to provide an antimicrobial composition comprising a grape extract, a lemon extract and a lavender extract as active ingredients.

As used herein, the term "antimicrobial" refers to the properties that resist microorganisms such as viruses, bacteria, fungi (for example, yeasts, molds, filamentous fungi, etc.), and more specifically the properties that inhibit or stop a growth or proliferation of the microorganisms, or promote or induce the death of the microorganisms. The term "antimicrobial activity" may be substituted therefor.

The term "extract" refers to a resulting product extracted using a proper extraction solvent. It should be understood that the resulting product includes an extraction solution, a diluent or concentrate of the extraction solution, a dried product obtained by drying the extraction solution, or a crude or purified product thereof, etc.

The term "grape extract" refers to an extract obtained from grapevine, for example, flowers, leaves, fruits, seeds, roots and/or stems of grapevine. The grapevine belongs to the order Rhamnales, the class Dicotyledoneae, and its scientific name may be *Vitis vinifera*. The grape extract may be preferably an extract obtained from the fruit of grapevine, more preferably an extract of the fruit skin of grapevine (hereinafter "grape skin").

The term "lemon extract" refers to an extract obtained from lemon tree, for example, flowers, leaves, fruits, seeds, roots and/or stems of lemon tree. The lemon tree belongs to the family Rutaceae, the order Geraniales, the class Dicotyledoneae, and its scientific name may be *Citrus limon*. Preferably, the lemon extract may be an extract obtained from the fruit of lemon tree.

The term "lavender extract" may be an extract obtained from flowers, leaves, fruits, seeds, roots and/or stems of lavender. The lavender belongs to the genus *Lavandula*, the family Lamiaceae, the order Lamiales, the class Dicotyledoneae. Preferably, the lavender extract may be an extract of flowers and/or leaves. More preferably, the lavender extract may be lavender oil obtained from flowers and/or leaves.

The extract may be prepared using any typical extraction method known in the art, for example, boiling extraction, hot water extraction, cold extraction, reflux cooling extraction, steam distillation extraction, alcohol extraction, ethanol extraction and/or ultrasonic extraction, etc. Preferably, the extract may be prepared using at least one extraction method selected among hot water extraction, cold extraction, steam distillation extraction and alcohol extraction. More preferably, the grape extract and lemon extract may be prepared according to a hot water extraction method, and the lavender extract may be prepared according to a steam distillation method.

The extraction solvent may be selected from the group consisting of water, lower alcohol having 1 to 4 carbon atoms (for example, methanol, ethanol, propanol, butanol, etc.), an organic solvent (hexane, acetone, chloroform, methyl acetate, etc.) and mixtures thereof. Preferably, the extraction solvent may be water.

The antimicrobial composition according to the present invention has antiviral, antibacterial and antifungal activities. More specifically, the composition according to the present invention exhibits an activity that inhibits, stops or delays the growth or proliferation of viruses, bacteria and fungi, an activity that promotes or induces the death thereof, an activity that inhibits infection therewith, etc.

The term "virus," as used herein, has the meaning generally understood in the art. As an unlimited example, it includes enterovirus, influenza virus etc. As the enterovirus, about 70 viruses including poliovirus, coxsackie A virus, coxsackie B virus, echovirus, enterovirus (EV) 71, etc. have been known up to now. In "Laboratory Diagnosis of Infectious Diseases" published by the Korea Centers for Disease Control and Prevention in 2005, it has been reported that enterovirus causes diverse symptoms such as silent infection, diarrhea, cold, hand-foot-mouth disease, herpangina, hemorrhagic conjunctivitis, poliomyelitis, meningitis, encephalitis, pneumonia, bronchitis, acute flaccid paralysis, myocarditis, etc. Enterovirus 71 causes aseptic meningitis, hand-foot-mouth disease, herpangina, acute hemorrhagic conjunctivitis, etc., and may cause severe complications in the brains or lungs, leading to death.

The term "bacteria," as used herein, has the meaning generally understood in the art. As an unlimited example, it includes Gram-positive bacteria such as *Staphylococcus* sp., Gram-negative bacteria such as *E. coli, Pseudomonas* sp., etc. It has been reported that examples of diseases and symptoms caused by the *Staphylococcus* sp. infection include, but not limited to, food poisoning, suppurative arthritis, suppurative osteomyelitis, folliculitis, tympanitis, conjunctivitis, pneumonia, postsurgical wound infection, bacteremia, sepsis, endocarditis, cellulitis, etc. It has been reported that examples of diseases and symptoms caused by the *E. coli* infection include, but not limited to, diarrhea, vomiting, fever, stomachache, headache, hemorrhagic enteritis, dehydration, hemolytic uremic syndrome (HUS), etc. It has been reported that examples of diseases and symptoms caused by the *Pseudomonas* sp. infection include, but not limited to, decubitus, pneumonia, bacteremia, sepsis, meningitis, keratitis, tympanitis, endocarditis, pyocephauls, etc.

The term "fungi" or "fungus," as used herein, has the meaning generally understood in the art. As an unlimited example, it includes yeasts such as *Candida*, filamentous fungi (also called molds), etc. It has been reported that examples of diseases and symptoms caused by the *Candida* yeast infection, but not limited to, stomatitis, vaginitis, vulvitis, esophagitis, paronychia, etc. It has been reported that examples of diseases and symptoms caused by the *Aspergillus* sp. infection include, but not limited to, tinea pedis, dermatophytosis, tinea cruris, dermatomycosis, etc.

The antimicrobial composition of the present invention comprises 0.01-99.98 wt % of a grape extract, 0.01-99.98 wt % of a lemon extract and 0.01-99.98 wt % of a lavender extract. Preferably, the composition may comprise 0.5 to 2 parts by weight of the lemon extract and 0.5 to 2 parts by weight of the lavender extract with respect to 1 part by weight of the grape extract. More preferably, the composition may comprise 0.5 to 1 parts by weight of the lemon extract and 0.5 to 1 parts by weight of the lavender extract with respect to 1 part by weight of the grape extract. Most preferably, the weight ratio of the active ingredients comprised in the composition may be grape extract:lemon extract:lavender extract=1:1:1. As a result of measurement of antimicrobial activity of the compositions according to the present invention, all the compositions mixing the active ingredients in various ratios exhibit significant antimicrobial effects. Particularly, it was confirmed that the composition in which the active ingredients are mixed in the same weight ratio (1:1:1) exhibits the most excellent antimicrobial activity.

Another aspect of the present invention is to provide a pharmaceutical composition comprising the antimicrobial composition.

In the pharmaceutical composition according to the present invention, the antimicrobial composition has the same meaning as described above, unless otherwise specified.

The pharmaceutical composition may be used for treating or preventing infection with microorganisms or diseases caused by infection with microorganisms.

The term "treat", "treating" or "treatment" refers to all actions that improve or cure microbial infection or symptoms or diseases caused by microbial infection by administering the composition according to the present invention. The term "prevent", "preventing" or "prevention" refers to all actions that inhibit or delay microbial infection or symptoms or diseases caused by microbial infection by administering the composition according to the present invention.

The pharmaceutical composition may be used for treating or preventing infection with at least one selected from the group preferably consisting of viruses, Gram-positive bacteria, Gram-negative bacteria, yeasts and filamentous fungi, or symptoms and diseases caused by such an infection.

The content of the antimicrobial composition comprised in the pharmaceutical composition according to the present invention may be appropriately adjusted depending on symptoms of diseases, progresses of symptoms, conditions of patients, etc. For example, the antimicrobial composition of the present invention may be contained in an amount of 0.0001 to 99.9 wt %, 0.1 to 90 wt %, 1 to 80 wt %, 1 to 70 wt %, 1 to 60 wt % or 1 to 50 wt % with respect to the total weight of the pharmaceutical composition.

The pharmaceutical composition of the present invention may further comprise a suitable carrier, excipient and/or diluent, which are commonly used in preparation of a pharmaceutical composition. Examples of the carrier, excipient and diluent which may be contained in the composition may include, but not limited to, lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil.

The pharmaceutical composition of the present invention may be a formulation for oral administration, or may be formulated into a formulation that is suitable for topical administration using a technique well known to a person having ordinary skill in the art. The formulation for topical administration may include external preparations, effervescent tablets, suppository preparations, etc. In one embodiment, the pharmaceutical composition of the present invention may be formulated into an external preparation by mixing the antimicrobial composition with a base that is well known and commonly used in the art. The external preparation may include emulsions, gels, ointments, creams, patches, liniments, powders, aerosols, sprays, lotions, serums, pastes, foams, drops, suspensions and tinctures.

The pharmaceutical composition of the present invention is administered to an individual in a pharmaceutically effective amount. The term "pharmaceutically effective amount," as used herein, refers to an amount sufficient to treat diseases at a reasonable benefit/risk ratio that is applicable to medical treatment. The effective dose level may be determined depending on factors including the type of individual and severity, age, gender, drug activity, sensitivity to drug, time of administration, route of administration and rate of release, duration of treatment, combined drugs, and other factors well known in the medical art. The composition of the present invention may be administered as an individual therapeutic agent or in combination with other therapeutic agents, may be administered sequentially or simultaneously with conventional therapeutic agents, and may be administered in a single or multiple doses. Taking all of the above factors into consideration, it is important to administer the pharmaceutical composition in an amount that can achieve the maximum effect with a minimum amount without side effects, and this can be easily determined by a person having ordinary skill in the art.

Another aspect of the present invention is to provide a cosmetic composition comprising the antimicrobial composition.

In the cosmetic composition according to the present invention, the antimicrobial composition has the same meaning as described above, unless otherwise specified.

The antimicrobial composition of the present invention may be contained in an amount of 0.0001 to 99.9 wt %, 0.1 to 90 wt %, 1 to 80 wt %, 1 to 70 wt %, 1 to 60 wt % or 1 to 50 wt % with respect to the total weight of the cosmetic composition.

The cosmetic composition can maximize antiviral, antibacterial, antifungal and detergent effects by containing the antimicrobial composition of the present invention. Accordingly, it can exhibit an effect of preventing or improving infection with microorganisms such as viruses, bacteria, fungi, etc. or diseases and symptoms caused by the microbial infection.

The term "improve", "improving" or "improvement" refers to all actions that at least reduce the microbial infection or parameters associated with the conditions of diseases caused thereby, for example, the severity of symptoms.

The cosmetic composition may be prepared in the form of typical emulsified formulation, solubilized formulation, etc. using any commonly known preparation method. Here, the composition may be appropriately selected and formulated depending on the desired purpose. For example, the composition may be prepared in diverse formulations such as toners, essences, creams, packs, patches, gels for skin adhesion, foundations, makeup bases, etc. and may be applied to any typical cosmetic preparation method.

The cosmetic composition may further comprise diverse optional additives in addition to the antimicrobial composition. Examples of the additive may include, but not limited to, at least one aqueous additive selected from stabilizers, emulsifiers, thickeners, humectants, liquid crystal film strengthening agents, pH regulators, antibacterial agents, water-soluble polymers, coating agents, metal ion sequestrants, amino acids, organic amines, polymer emulsions, pH adjusters, skin nutrients, antioxidants, synergists, preservatives, fragrances, etc.; and at least one nonaqueous additive selected from fats and oils, waxes, hydrocarbon oils, higher fatty acid oils, higher alcohols, synthetic ester oils and silicone oils, etc.

Another aspect of the present invention is to provide a food composition comprising the antimicrobial composition.

In the food composition according to the present invention, the antimicrobial composition has the same meaning as described above, unless otherwise specified.

The food composition may improve or prevent infection with microorganisms such as bacteria, viruses, yeasts and molds, etc. or diseases caused by the microbial infection.

The term "improve", "improving" or "improvement" refers to all actions that at least reduce the microbial infection or parameters associated with the conditions of diseases caused thereby, for example, the severity of symptoms.

The food may be health functional food. The term "health functional food" refers to food prepared and processed in the form of tablets, capsules, powders, granules, liquids, pills, etc., using raw materials or ingredients having functionality useful to the human body. Here, the term "functional" means obtaining useful effects for health use such as nutrient control or physiological action on the structure and function of the human body.

The food composition according to the present invention may be prepared according to any method commonly used in the art, and may add raw materials and ingredients commonly used in the art when prepared. The food composition of the present invention comprises natural plant extracts as main active ingredients, and thus has no side effects or harm to the human body. Accordingly, the composition may also be taken as a supplement for promoting or improving the treatment effect of microbial infection or diseases caused thereby.

The content of the antimicrobial composition comprised as an active ingredient in the food composition according to the present invention may be determined appropriately depending on the use purpose such as prevention, improvement or therapeutic treatment. In general, when preparing food, the antimicrobial composition of the present invention may be comprised in an amount of 0.001 to 20 wt %, 0.001 to 15 wt % or 0.001 to 10 wt % in the raw composition. For health beverage, the composition may be added in an amount of 0.01 to 2 mg, for example, 0.3 to 1 mg, based on the amount of 100 mL. However, for long-term intake with the purpose of health and hygiene or the purpose of health control, the composition may be used in an amount less than the range aforementioned. The content of the antimicrobial composition added during the process of preparing the food composition may be appropriately adjusted depending on any needs.

The food composition may be any formulation selected from the group consisting of pills, tablets, granules, powders, capsules and liquids.

Another aspect of the present invention is to provide a quasi-drug comprising the antimicrobial composition.

In the quasi-drug according to the present invention, the antimicrobial composition has the same meaning as described above, unless otherwise specified.

Since the antimicrobial composition of the present invention has very strong inhibitory activity on viruses, bacteria and fungi, it may be used as a quasi-drug for anti-microorganism. In addition, it may be safely used without toxicity and harmfulness to the human body since the active ingredients therein are derived from plants.

The term "quasi-drug," which excludes a product used for drug, refers to a fiber, rubber product and the like used for the purpose of treating, alleviating, curing or preventing diseases of humans or animals; a product that is not an apparatus or machine, weakly acting on the human body or not directly acting on the human body; or a product used for sterilization, insecticide and similar purposes for prevention of infection. It includes, for examples, disinfectants, sterilizing detergents, personal care products, etc.

The quasi-drug according to the present invention may be used as disinfectants, detergents, etc. For the disinfectant, the antimicrobial composition of the present invention may be used as it is, or by diluting with a dermatologically or pharmaceutically acceptable diluent or solvent so as to be a proper concentration. The disinfectant may be used to the surface of living subject, preferably to the skin of mammals, most preferably to the skin of humans. For example, the disinfectant may be prepared and used in the form of ointment preparations, lotion preparations, spray preparations, patch preparations, cream preparations, powder preparations, suspension preparations or gel preparations. In addition, the disinfectant may be used to the surface of non-living subject, for example, the surface of tree, metal, glass, ceramic, plastic, paper or cloth. The disinfectant may be treated to the surface of the living or non-living subjects using a method including immersing, swabbing, spraying and brushing. Preferably, the disinfectant may be used in hospitals and houses for the use of disinfection of the surface of wounds, skin before surgery, surgical instruments, conduits, etc. For the sterilizing detergent, it may be easily prepared according to any method known in the art by comprising at least one excipient or additive generally used in the field of preparation of detergents, in addition to the antimicrobial composition according to the present invention. The detergent may be used for kitchen or food. The detergent for kitchen may further comprise anionic surfactants, non-ionic surfactants, amphoteric surfactants, etc. in addition to processed citraconic anhydrides. The detergent for food may be prepared by adding a solvent or diluent acceptable in the field of food to the antimicrobial composition in order to dilute the detergent at a proper concentration, and may be used for disinfecting and cleaning, for example, fruit, fish, meat, etc. In addition, the quasi-drug may be personal care products, for example, soaps, cosmetics, wet wipes, tissues, shampoos, skin creams, facial creams, toothpastes, cleansing gels, etc.

A mixture composition containing a grape extract, a lemon extract and a lavender extract as active ingredients can effectively inhibit viruses, bacteria, yeasts and filamentous fungi in a short time. Thus, the composition of the present invention provides excellent antiviral, antibacterial and antifungal effects. In addition, the composition is derived from natural products, and thus can be safely used without toxicity and side effects in various applications such as drug products, foods, cosmetic products, quasi-drugs, etc.

The articles "a" and "an" are used herein to refer to one or to more than one (i.e. to at least one) of the grammatical object of the article. By way of example, "an ingredient" means one ingredient or more than one ingredient.

BRIEF DESCRIPTION OF FIGURES

FIG. 1 is a graph indicating the inhibitory effect on enterovirus 71 for each active ingredient and mixture containing the active ingredients in various ratios.

FIG. 2 is a Western blot result showing the levels of VP proteins of enterovirus 71 in the case of treatment with the compositions of the present invention.

EXAMPLES

In the following, exemplary embodiments of the inventive concept will be explained in further detail with reference to examples. However, the following examples are meant to exemplify the present invention, and the scope of the invention is not restricted by these examples.

Example 1. Preparation of Grape Extract 30 g of dried grape skin was immersed in 570 g of water, and then subjected to hydrothermal treatment (under reflux) in an extraction apparatus having a cooling condenser under the conditions of 60° C. for 1 hour. After completion of hydrothermal treatment (under reflex), the treated grape skin was centrifuged using a centrifuge (Supra 22K, Hanil, Korea) under the conditions of 8,000 rpm and 15° C. for 20 minutes to separate an extract. The separated extract was filtered with 0.8 μm and 0.45 μm filters to obtain a filtrate. The filtrate was concentrated using a concentration apparatus (Rotary Evaporator NE-series, Eyela, Japan) under the conditions of 60° C. and 30 hPa for 2 hours. The concentrate was prelyophilized under the conditions of −21° C., and then lyophilized using a lyophilizer (Bondiro, Ilshin, Korea) at −80° C. for 48 hours to obtain an extract. The resultant grape extract was referred to as "Sample 1" and used in the following test examples.

Example 2. Preparation of Lemon Extract 30 g of dried lemon was immersed in 570 g of water, and then the same method as described in Example 1 above was used to obtain a lemon extract. The resultant lemon extract was referred to as "Sample 2" and used in the following test examples.

Example 3. Preparation of Lavender Extract 30 g of dried lavender was put in a steam distillation extraction set containing 570 g of water, and then subjected to steam distillation extraction in an essential oil extraction apparatus having a cooling condenser under the conditions of 100° C. for 1 hour. The steam distillation extract obtained by cooling was cooled at 5° C. and left to stand for 24 hours to obtain separated oil from the upper layer. The resultant lavender oil was referred to as "Sample 3" and used in the following test examples.

Example 4. Preparation of Mixture Compositions of Grape Extract, Lemon Extract and Lavender Extract The grape extract, lemon extract and lavender extract obtained in Examples 1, 2 and 3 above, respectively, were mixed in weight ratios of 1:1:1, 2:1:1, 1:2:1 and 1:1:2 using a homogenizer (IKA T25, IKA, JPN) to obtain four mixture compositions. The resultant mixture compositions were referred to as "Sample 4," "Sample 5," "Sample 6," and "Sample 7" in the order of the weight ratios of 1:1:1, 2:1:1, 1:2:1 and 1:1:2, respectively, and used in the following test examples.

Test Example 1. Inhibitory Effect on Enterovirus 71 Infection 1-1. Measurement of Antiviral Activity Using SRB Assay In order to confirm the inhibitory effect of the composition according to the present invention on enterovirus 71 infection, the test was conducted by applying sulforhodamine B (SRB) assay (Choi et al, Antiviral activity of raoulic acid from *Raoulia australis* against Picornaviruses, Phytomedicine, 2009).

Vero cells were seeded into well-plates at a concentration of $3 \times 10^4$ cell/well and cultured for 24 hours using DMEM media containing 10% FBS. After removing the media and washing with PBS, enterovirus 71 suspension and FBS media were added to wells containing the samples prepared in Examples above at a concentration of 100 μg/mL, and then the cells were cultured in a $CO_2$ incubator (Sanyo, JPN) in 5% $CO_2$ condition for two days. Thereafter, they were washed with PBS, and 100 μl of 70% acetone was added to each well, left at room temperature for 30 minutes, and then removed. After drying the well using a dry oven (Hanbaek, KOR) for 10 minutes, 100 μl of 0.4% SRB dye containing 1% acetic acid was added thereto and left at room temperature for 30 minutes. The SRB was removed, and the plates were washed several times with cosolvents containing 1% acetic acid, followed by drying again using a dry oven. A phase-contrast microscope (Nikkon, JPN) was used for observation. Each dyed well was dissolved with Tris-base solution and left. Then, optical density (OD) values were measured at 560 nm using an ELISA reader (EPOCH2, Biotek, USA).

The optical density (OD) values as measured were included in the following Equation 1 to calculate the antiviral activity rates of Samples 1 to 7 in percentage. Here, the antiviral activity rate means the activity that the samples inhibit the growth and proliferation of enterovirus 71, which may be also construed that the activity rate means the rate of cell protection against enterovirus 71 infection.

$$\frac{OD(\text{Experimental group treated wtih virus+sample}) - OD(\text{Control group treated wtih virus})}{OD(\text{Control group untreated with virus}) - OD(\text{Control group treated wtih virus})} \times 100 =$$

antiviral activity rate (%) [Equation 1]

Figure 1:
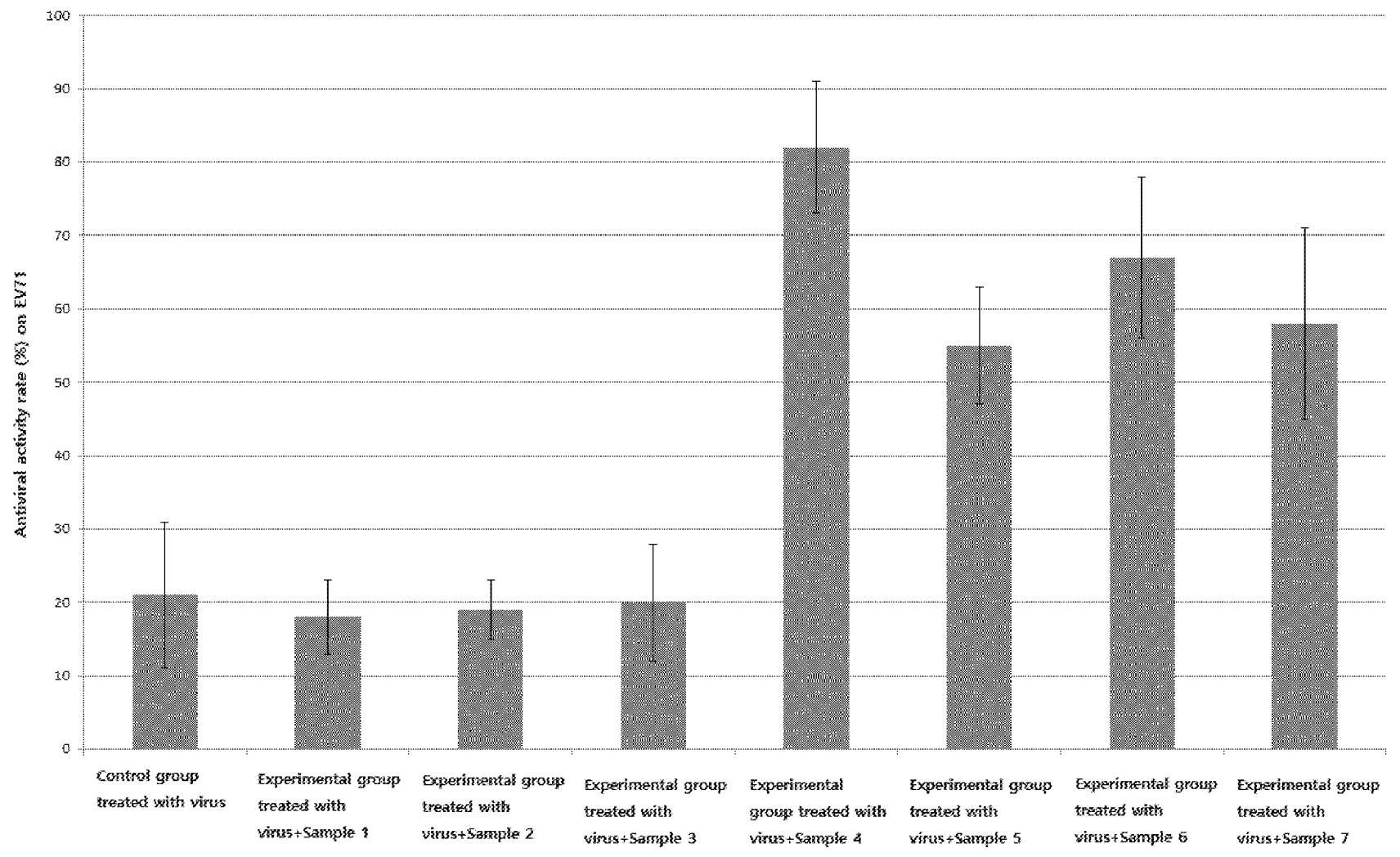

The antiviral activity rate (%) of each composition, calculated according to Equation 1 above, is shown in graph of FIG. 1. As can be seen from FIG. 1, it was confirmed that the compositions comprising the respective single extracts alone (Samples 1, 2 and 3) have little cell protective effect against enterovirus 71 infection. In contrast, it could be confirmed that all of the mixture compositions (Samples 4, 5, 6 and 7) show significant cell protective effects against enterovirus 71 infection, irrespective of the mixing ratios. Particularly, it was observed that the composition (Sample 4) in which the grape extract, lemon extract and lavender extract are mixed in a ratio of 1:1:1 exhibits the most excellent antiviral activity.

1-2. Confirmation of Antiviral Activity Through Western Blot Analysis of VP Proteins In order to re-verify the antiviral efficacy of the compositions according to the present invention, Western blotting was performed for VP0 capsid protein of enterovirus 71.

The supernatant containing VP0 capsid protein of enterovirus 71 was subjected to electrophoresis on acrylamide gels, and then moved to iBlot Transfer Stack, PVDF, regular size (IB401001, invitrogen). The membranes were reacted with 5% skim milk (232100, Difco) at room temperature for 1 hour, and then washed 3 times with phosphate buffered saline (PBS) Tween-20.

Thereafter, a mouse anti-enterovirus 71 monoclonal antibody (MAB 979, Millipore) as a primary antibody was reacted with the membranes at room temperature for 2 hours, and then washed several times with PBS Tween-20. For α-tubulin, a mouse IgG1 monoclonal antibody (SC-32293, Santa Cruz) was used as a primary antibody.

As a secondary antibody for detecting VP proteins of enterovirus 71 and α-tubulin, polyclonal goat anti-mouse IgG(H+L) HRP (SA001-500, GenDEPOT) was used. The polyclonal goat anti-mouse IgG(H+L) HRP was diluted 5,000 times in 5% skim milk, reacted with the membranes at room temperature for 1 hour, and washed with PBS Tween-20, to perform the Western blot.

As can be seen from FIG. 2, α-tubulin was detected in all the control group untreated with virus, control group treated with virus and experimental groups treated with virus+sample. VP0 capsid protein of enterovirus 71 was not shown in the control group untreated with virus, whereas the proteins were very distinctly shown in the control group treated with virus. VP0 capsid protein of enterovirus 71 was hardly observed in the experimental group treated with Sample 4 falling under the present invention. In addition, VP0 capsid protein of enterovirus 71 was partially detected in the experimental groups treated with Sample 5, 6 or 7 falling under the present invention, but observed at very low detection levels as compared with the control group treated with virus.

Accordingly, it was demonstrated that when the compositions according to the present invention are treated against viruses, significant levels of antiviral activity are exhibited. Particularly, the composition in which the grape extract, lemon extract and lavender extract are mixed in a ratio of 1:1:1 exhibits the most excellent antiviral activity.

Test Example 2. Antiviral Effects Against Influenza a Virus

In order to test the antiviral effects of the compositions according to the present invention, the experiments on Influenza A virus were conducted by the Virus Research and Testing Center of Korea Research Institute of Chemical Technology, which is a Korean government-funded research institute.

As for the control group in this experiment, Influenza A virus (H3N2) and water were mixed in a volume ratio of 1:9 and reacted at room temperature (approximately 23° C.). Each virus titer was measured after 5 minutes and 60 minutes to determine the Virus reduction.

As for the experimental group, Influenza A virus (H3N2) and the composition of the present invention in the form of liquid (Sample 4) were mixed in a volume ratio of 1:9 and reacted at room temperature (approximately 23° C.). Each virus titer was measured after 5 minutes and 60 minutes to determine the Virus reduction.

TABLE 1

| | Virus titer (CCID$_{50}$/well) | | Virus reduction (%) | |
| --- | --- | --- | --- | --- |
| | After 5 min reaction | After 60 min reaction | After 5 min reaction | After 60 min reaction |
| Control Group | 2,658,000 | 2,658,000 | — | — |
| Experimental Group | <316 | <316 | >99.988% | >99.988% |

As can be confirmed from Table 1, the composition of the present invention made more than 99.9% of Influenza A virus to be inactive even within a very short period of time such as five minutes, thereby proving its strong antiviral effects.

Test Example 3. Antibacterial and Antifungal Effects

In order to test an antibacterial activity and an antifungal activity of the samples obtained in Examples above, experiments according to agar serial dilution method and paper disc method were conducted.

A total of 5 types of strain, *Staphylococcus aureus* (KCTC 6910) as Gram-positive bacteria, *Pseudomonas aeruginosa* (KCTC 1637) and *E. Coli* (KCTC 1039) as Gram-negative bacteria, *Candida albicans* (KCTC 7965) as yeasts and *Aspergillus niger* (KCTC 6910) as filamentous fungi, were used, and they were all sold from the Korea Research Institute of Bioscience and Biotechnology. Specific experimental methods and results are as follows.

3-1. Experiment According to Agar Serial Dilution Method

The antimicrobial activity of the compositions was confirmed by measuring the minimum inhibitory concentration according to agar serial dilution method.

In order to conduct antimicrobial tests, the bacteria was inoculated into a tryptic soy agar medium to preincubate at 37° C. for 24 hours; the yeasts was inoculated into a potato dextrose agar medium to preincubate at 25° C. for 2 days; and the filamentous fungi was inoculated into a potato dextrose agar medium to preincubate at 25° C. for 7 days, and then the spores of filamentous fungi formed on the surface of the medium were collected using a spreader and diluted in sterile saline solution for use.

2 mL of the composition diluted with 5% dimethyl sulfoxide (DMSO) physiological saline solution was added to each sterilized Petri dish. 5% DMSO physiological saline solution was used as a control group. 18 mL of each tryptic soy agar medium and potato dextrose agar medium sterilized was added to each Petri dish, followed by stirring, and then left to stand to be coagulated.

Thereafter, each strain preincubated was spread on Petri dish (spread cell concentration: about 1×10$^6$ CFU/mL of bacteria; about 1×10$^5$ CFU/mL of yeasts; and about 1×10$^4$ CFU/mL of filamentous fungi). The bacteria were incubated at 37° C. for 24 hours, the yeasts were incubated at 25° C. for 3 days, and the filamentous fungi were incubated in a 25° C. incubator for 7 days. Thereafter, the formation of colonies in each compartment was observed.

The minimum sample concentration (i.e., minimum inhibitory concentration (MIC)) of the not-grown plates was determined, and the results are shown in Table 2 below. Here, the smaller MIC value indicates the higher antimicrobial effect.

TABLE 2

| | MIC (μg/mL) | | | | | | |
| --- | --- | --- | --- | --- | --- | --- | --- |
| Strain | Sample 1 | Sample 2 | Sample 3 | Sample 4 (mixing ratio 1:1:1) | Sample 5 (mixing ratio 2:1:1) | Sample 6 (mixing ratio 1:2:1) | Sample 7 (mixing ratio 1:1:2) |
| *S. aureus* | >5,000 | 5,000 | 500 | 100 | 150 | 100 | 200 |
| *P. aeruginosa* | >5,000 | >5,000 | 1,000 | 100 | 200 | 150 | 150 |
| *E. Coli* | >5,000 | >5,000 | 750 | 75 | 200 | 100 | 100 |
| *C. albicans* | >5,000 | >5,000 | 1,000 | 50 | 100 | 150 | 100 |
| *A. niger* | >5,000 | >5,000 | 2,000 | 200 | 250 | 300 | 200 |

As can be confirmed from Table 2, all the mixture compositions of the present invention exhibited strong antimicrobial effects on various kinds of bacteria, yeasts and filamentous fungi as compared with the single extracts.

3-2. Experiment According to Paper Disc Method

In order to test the antimicrobial effect of the compositions, experiments according to paper disc method were conducted.

The strain incubated in each plate medium was taken in an amount of one platinum loop and incubated in 10 mL liquid medium for 24 hours for activation. 0.1 mL of the microbial solution incubated in the 10 mL liquid medium was further incubated for 6 hours, and then the microbial solution was inoculated into each plate medium so as to be about 10$^7$ CFU/mL, and uniformly spread. Thereafter, sterile paper discs (6 mm, Satorius, Germany) were placed on solid plate media, and then the samples dissolved in a solvent were absorbed to be 0.05 ml/disk and incubated. *Staphylococcus aureus, Pseudomonas aeruginosa* and *E. Coli* were incubated at 37° C.; and *Candida albicans* and *Aspergillus niger*, which are types of fungus, were incubated at 27° C. for 24 hours and 120 hours, respectively. And then, the diameters of the transparent zones around the paper disks were measured.

The results of measurement are shown in Table 3 below. Here, the transparent zone around the paper disk is an index indicating the inhibition degree of proliferation of the corresponding strain. Accordingly, the greater diameter (mm) of the transparent zone indicates the higher antimicrobial effect on the strain.

TABLE 3

| | Transparent zone diameter (mm) | | | | | | |
|---|---|---|---|---|---|---|---|
| Strain | Sample 1 | Sample 2 | Sample 3 | Sample 4 (mixing ratio 1:1:1) | Sample 5 (mixing ratio 2:1:1) | Sample 6 (mixing ratio 1:2:1) | Sample 7 (mixing ratio 1:1:2) |
| S. aureus | — | 8 | 15 | 24 | 22 | 23 | 18 |
| P. aeruginosa | — | — | 12 | 24 | 21 | 22 | 20 |
| E. Coli | — | — | 13 | 30 | 20 | 25 | 20 |
| C. albicans | — | — | 11 | 35 | 22 | 20 | 20 |
| A. niger | — | — | 8 | 22 | 18 | 16 | 18 |

As shown in Table 3, Sample 1 and Sample 2, which are single extracts, have little antimicrobial effect, and Sample 3 partially exhibits antimicrobial effect. On the other hand, all the mixture compositions show significantly excellent antimicrobial effects on various kinds of bacteria, yeasts and filamentous fungi as compared with the single extracts. Particularly, it was confirmed that Sample 4 at a mixture ratio of 1:1:1 exhibits the most excellent antibacterial and antifungal effects.

Hereinafter, toner and lotion are provided as formulation examples of the present invention. However, these should not be construed as limiting the formulation of the composition according to the present invention. Additionally, a person having ordinary skill in the art may make any modifications within the scope of the present invention.

TABLE 4

Formulation example 1. Toner

| | Ingredient | Content (%) |
|---|---|---|
| 1 | Purified water | residual quantity |
| 2 | Butylene glycol | 5.00 |
| 3 | Composition of the present invention | 2.00 |
| 4 | Glycerine | 4.00 |
| 5 | Disodium EDTA | 0.02 |
| 6 | Carbomer | 0.10 |
| 7 | Betaine | 0.50 |
| 8 | Hyaluronic acid | 0.01 |
| 9 | Ethanol | 4.00 |
| 10 | PEG-60 hydrogenated castor oil | 0.30 |
| 11 | Methylparabene | 0.10 |
| 12 | Phenyl trimethicone | 0.05 |
| 13 | Fragrance ingredient | trace |
| 14 | Coloring agent | trace |

TABLE 5

Formulation example 2. Lotion

| | Ingredient | Content (%) |
|---|---|---|
| 1 | Purified water | residual quantity |
| 2 | Methylparabene | 0.20 |
| 3 | Composition of the present invention | 5.00 |
| 4 | Glycerine | 5.00 |
| 5 | Butylene glycol | 7.00 |
| 6 | Carbomer | 0.10 |
| 7 | Xantan gum | 0.05 |
| 8 | Cetearyl alcohol | 3.00 |
| 9 | Glyceryl stearate | 0.50 |
| 10 | Propylparaben | 0.10 |
| 11 | Mineral oil | 3.00 |
| 12 | Plant squalene | 3.00 |
| 13 | Cetyl ethylhexanoate | 3.00 |
| 14 | Arginine | 0.10 |
| 15 | Fragrance | trace |

TABLE 6

Formulation example 3. Cream

| | Ingredient | Content (%) |
|---|---|---|
| 1 | Purified water | residual quantity |
| 2 | Methylparabene | 0.20 |
| 3 | Composition of the present invention | 5.00 |
| 4 | Glycerine | 5.00 |
| 5 | Butylene glycol | 7.00 |
| 6 | Carbomer | 0.20 |
| 7 | Xantan gum | 0.08 |
| 8 | Cetearyl alcohol | 3.00 |
| 9 | Glyceryl stearate | 0.50 |
| 10 | Behenyl alcohol | 2.00 |
| 11 | Hydrogenated lecithin | 0.20 |
| 12 | Propylparaben | 0.10 |
| 13 | Mineral oil | 3.00 |
| 14 | Plant squalene | 3.00 |
| 15 | Cetyl ethylhexanoate | 3.00 |
| 16 | Arginine | 0.20 |
| 17 | Fragrance | trace |

TABLE 7

Formulation example 4. Essence

| | Ingredient | Content (%) |
|---|---|---|
| 1 | Purified water | residual quantity |
| 2 | Methylparabene | 0.20 |
| 3 | Composition of the present invention | 5.00 |
| 4 | Hyaluronic acid | 0.05 |
| 5 | Butylene glycol | 2.00 |
| 6 | Carbomer | 0.08 |
| 7 | Xantan gum | 0.04 |
| 8 | Cetearyl alcohol | 0.50 |
| 9 | Glyceryl stearate | 0.50 |
| 10 | Propylparaben | 0.10 |
| 11 | Mineral oil | 1.00 |
| 12 | Plant squalene | 2.00 |
| 13 | Cetyl ethylhexanoate | 1.00 |
| 14 | Arginine | 0.08 |
| 15 | Ethanol | 4.00 |
| 16 | PEG-60 hydrogenated castor oil | 0.30 |
| 17 | Fragrance | trace |

TABLE 8

Formulation example 5. Face pack

| | Ingredient | Content (%) |
|---|---|---|
| 1 | Purified water | residual quantity |
| 2 | Glycerin | 10.00 |
| 3 | Composition of the present invention | 5.00 |
| 4 | Butylene glycol | 5.00 |
| 5 | Kaolin | 4.00 |
| 6 | Caprylic/capric triglyceride | 4.00 |
| 7 | Cyclomethicone | 1.00 |
| 8 | Magnesium aluminum silicate | 1.00 |

TABLE 8-continued

Formulation example 5. Face pack

| | Ingredient | Content (%) |
|---|---|---|
| 9 | PEG-100 stearate, glyceryl stearate | 2.00 |
| 10 | Xantan gum | 0.10 |
| 11 | Ethanol | 3.00 |
| 12 | Methylparabene | 0.20 |
| 13 | Chlorphenesin | 0.10 |
| 14 | Titanium dioxide | 0.50 |
| 15 | Fragrance | trace |

What is claimed is:

1. A method for treatment or prevention of infection with Enterovirus 71 or diseases caused by the infection with Enterovirus 71, comprising:
administering an antimicrobial composition comprising a grape extract, a lemon extract and a lavender extract as active ingredients to a subject in need thereof,
wherein the antimicrobial composition comprises the grape extract, the lemon extract and the lavender extract in a weight ratio of 1-2:1-2:1-2.

2. A method for inhibiting activity or infection of Enterovirus 71, comprising:
applying an antimicrobial composition comprising a grape extract, a lemon extract and a lavender extract as active ingredients to an area in need thereof,
wherein the antimicrobial composition comprises the grape extract, the lemon extract and the lavender extract in a weight ratio of 1-2:1-2:1-2.

3. The method of claim 1, wherein the grape extract is obtained from grape skin.

4. The method of claim 1, wherein the lavender extract is lavender oil.

5. The method of claim 2, wherein the grape extract is obtained from grape skin.

6. The method of claim 2, wherein the lavender extract is lavender oil.

* * * * *